United States Patent [19]

Burton

[11] Patent Number: 4,835,253

[45] Date of Patent: May 30, 1989

[54] SPECIFIC INHIBITORS OF TISSUE KALLIKREIN

[75] Inventor: James A. Burton, Jamaica Plain, Mass.

[73] Assignee: The University Hospital, Boston, Mass.

[21] Appl. No.: 33,974

[22] Filed: Apr. 3, 1987

[51] Int. Cl.⁴ .............................. C07K 5/08; C07K 5/10
[52] U.S. Cl. ..................................... 530/330; 530/331
[58] Field of Search ........................... 530/329; 514/12

[56] References Cited

PUBLICATIONS

Chem. Abstr. vol. 89, (1978) 38634.
Chem. Abstr. vol. 92 (1980) 193364.
Chem. Abstr. vol. 99 (1983) 35031.
Chem. Abstr. vol. 106 (1987) 152095.
Chem. Abstr. vol. 103 (1985) 34004.
Chem. Abstr. vol. 105 (1986) 74765.

*Primary Examiner*—Delbert R. Phillips
*Attorney, Agent, or Firm*—David Prashker

[57] ABSTRACT

A unique class of tissue kallikrein inhibitors is provided which are specific for tissue kallikreins and do not substantially cross-react with plasma kallikreins or other serine proteases in-vivo. These inhibitors are substrate analogues of low molecular weight kininogens but are highly inhibitory, stable and resistant to enzymatic hydrolysis, and release non-toxic degradation products.

16 Claims, 2 Drawing Sheets

SPECIFIC INHIBITORS OF TISSUE KALLIKREIN

FIELD OF THE INVENTION

The present invention is concerned with compositions and therapeutic methods for controlling blood pressure and is particularly directed to novel compositions which are specific inhibitors of tissue kallikreins for the treatment of hypotension, for reversing the consequential side-effects produced by neutralization of angiotensin converting-enzyme, and a variety of other clinical/therapeutic applications.

BACKGROUND OF THE INVENTION

The plasma kinins—kallidin and bradykinin—are polypeptides produced in-vivo which possess an extrordinarily high degree of pharmacological activity. They are the most potent vasodilator autacoids of mammals. In very low concentration they increase capillary permeability; produce edema; evoke pain and reflexes by acting on nerve endings; contract or relax various smooth muscles; and elicit various other responses in the body. In all these respects, bradykinin and kallidin behave very similarly.

These vasoactive kinins are cleaved from polypeptide or proteinl precursors in the plasma $a_2$-globulin fraction known as kininogens. This cleavage is the result of a select group of serine proteases, collectively referred to as kininogenases—of which the best known are the kallikreins; a group of enzymes of high substrate specificity that are present in plasma, in body tissues such as kidney and in various exocrine glands such as the pancreas. The specificity of each kallikrein is very high: plasma kallikreins release the nonapeptide kinin, bradykinin, directly from a kininogen of high (approximately 100,000 daltons) molecular weight (hereinafter "HMW kininogen"). Glandular and other tissue kallikreins release the decapeptide kinin, kallidin, from a kininogen of low (approximately 50,000 daltons) molecular weight (hereinafter "LMW kininogen"). Other proteolytic enzymes such as trypsin can release kinins non-specifically from various kininogens. Trypsin, however, does not circulate in the body and tissue kallikreins are believed to be the natural source of circulating kallekreins.

The kinins, bradykinin and kallidin, once produced, have a very short existence; their half-life in plasma is only about 15 seconds. The principle reason for their destruction in-vivo is the dipeptidyl carboxypeptidase known in this context as kininase II and in most other circumstances as angiotensin converting-enzyme (hereinafter "ACE"). This angiotensin converting enzyme is now well recognized as being responsible for the conversion of angiotensin I to the active angiotensin II which is directly involved in hypertension and debilitating hypertensive conditions. With the rise and use of effective anti-hypertensive drugs such as enalapril and captopril which act directly to inhibit ACE and markedly decrease production of angiotensin II, the consequential side-effect has been to unintensionally increase the quantities of vasoactive kinins circulating in the body. Thus, by acting affirmatively to control hypertension by inhibiting the enzymatic activity of ACE, this has resulted directly in unwanted and undesirable quantities of active kinins which react adversely in-vivo.

In addition to the foregoing problem, the capacity of human urinary kallikrein (a glandular kallikrein) to produce active kinin peptides has been of major concern in the intrarenal regulation of blood pressure [Levinsky, N. G., Circ. Res. 44: 441–451 (1979)]. One prevalent view is that kinin production in the kidneys is a major influence over if not a cause of, clinically observable hypotension and ortho-static hypotension. Equally important, recent reports have described urinary kallikrein and kallikrein-like proteases to function in the processing of prohormones or proenzymes such as prorenin, proinsulin, atriopeptigen, tissue plasminogen activator, nerve growth factors, and epidermal growth factors. For both clinical and research purposes, therefore, compounds demonstrating specific activity as kallikrein inhibitors continue to be sought.

Recently, a variety of kinin analogues having some kinin-like activity were evaluated. The kinins may act either directly on the vascular smooth muscle or indirectly by causing the release of endoplasmic derived relaxing factors (EDRF) from the vascular intima [Stewart, J. M. in *Handbook Of Experimental Pharmacology*, Volume 25 (supplement), New York, Springer-Verlag, 1979, pages 227–285]. Subsequently, a series of protease inhibitors which were not specific for glandular kallikreins and often possess undesirable biological activity themselves (such as the ability to induce hypotension) were evaluated. These included: aprotinin [Fritz et al., *Fed. Proc.* 38: 2753–2759 (1979); Seto et al., *Hypertension* 5: 893–899 (1983)]; benzamidine [Vogel, R., "Kallikrein Inhibitors", in *Handbook Of Experimental Pharmacology*, Volume 25 (supplement), New York, 1979, pages 163–225]; aromatic diamidines [Geratz, J. D., *J. Med. Chem.* 16: 970–973 (1973); Geratz, et al., *Arch. Int. Pharm. Ther.* 194: 359–370 (1971)]; and peptides of arginine chloromethyl ketones [Kettner et al., *Arch. Biochem. Biophys.* 202: 420–430 (1980)]. Even more recently, there has been some investigation of substrate analogues based on the amino acid sequence of bovine kininogen and the capacity of such analogues to inhibit human urinary kallikrein [Okunishi et al., *Hypertension* 7 (suppl. I): I-72-I-75 (1985)]. Despite this accumulated body of knowledge, there remains the continuing problem of developing highly specific kallikrein inhibitors which are not rapidly cleaved and degraded; and which are demonstratably functional in-vivo to inhibit the activity of glandular kallikreins.

SUMMARY OF THE INVENTION

The present invention is a substrate analogue class of tissue kallikrein inhibitors comprising the formula

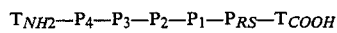

$$T_{NH_2}-P_4-P_3-P_2-P_1-P_{RS}-T_{COOH}$$

wherein $P_1$ is an arginine residue or an effective arginine residue substitute;

$P_2$ is an amino acid residue comprising at least one ring configuration in its structure;

$P_3$ is selected from the group consisting of a branched amino acid residue without any ring configuration in its structure; an amino acid residue comprising an least 5 and not more than 15 carbon atoms and having at least one alicyclic or aromatic ring configuration in its structure; a branched or alicyclic aliphatic compound comprising at least 5 and not more than 15 carbon atoms in its structure; and an organic composition comprising at least 5 and not more than 15 carbon atoms and having at least one aromatic ring configuration in its structure;

$P_4$ can be omitted entirely, but when present is a linear amino acid;

$T_{COOH}$ can be omitted entirely, but when present is a moiety bound to the carboxy terminal end of the inhibitor molecule which affects the physical properties of the inhibitor; and $T_{NH2}$ can be omitted entirely, but when present is a moiety bound to the N-terminal end of the inhibitor molecule and which affects the physical properties of the inhibitor.

DETAILED DESCRIPTION OF THE DRAWING

The present invention may be more completely and easily understood when taken in conjunction with the accompanying drawing, in which.

DETAILED DESCRIPTION OF THE PREFERRED EMBODIMENTS

Figure 1:
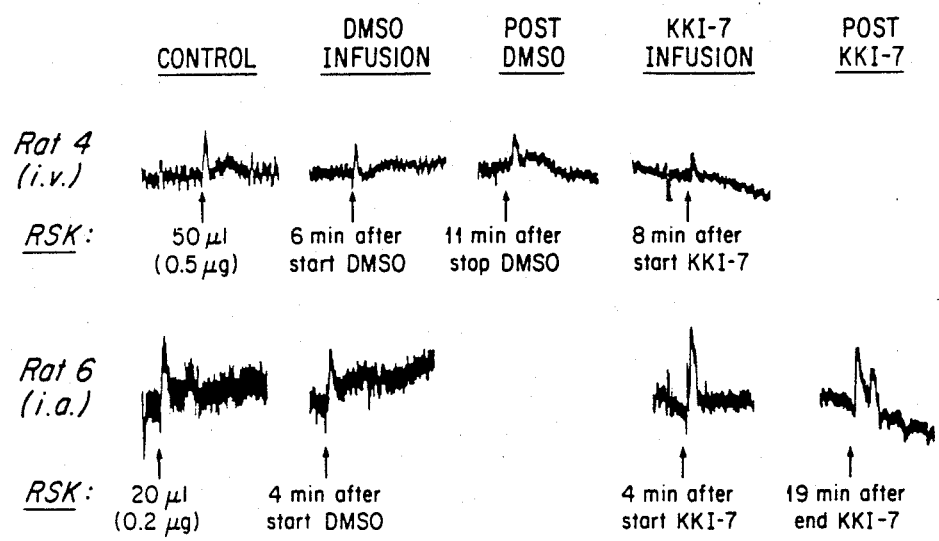
FIG. 1 is a series of representative tracings of femoral artery blood flow responses to rat submaxillary gland kallikrein injected before, during, and after the infusion of KKI-7 inhibitor or DMSO vehicle.

The present invention is a class of competitive inhibitors which are specific for tissue or glandular kallikreins but does not inhibit the activity of plasma kallikreins or other serine proteases in the body. These specific tissue kallikrein inhibitors are unique substrate analogues which have been devised and prepared based upon the naturally occuring amino acid sequence surrounding the arginine-serine cleavage site of bovine kininogen—an amino acid sequence which has been well documented [Nawa et al., *Proc. Natl. Acad. Sci.* USA 80: 90–94 (1983) ]. A very preliminary report identifying the suitability of the substrate analogue approach to designing specific kallikrein inhibitors has been made [Okunishi et al., *Hypertension* 7 (suppl. I): I-72–I-75 (1985)]. This reported group of acetyl-peptidylamides able to inhibit human urinary kallikrein retains the naturally occuring amino acid sequences of bovine kininogen and identifies the effect of differences in peptide length among tetrapeptide, pentapeptide, hexapeptide, and heptapeptide naturally occuring sequences.

In contrast to this preliminary information, the present invention provides an elaborate series of artificially synthesized amino acid sequences which do not occur in nature; are not rapidly degraded by the tissue kallikreins; and demonstrate considerably greater inhibitory potency and specificity for tissue kallikreins. The present invention is also unique in its demonstration of in-vivo effectiveness within animal systems.

These unique substrate analogue inhibitors are specific against tissue kallikreins thus provide major advantages and uses not previously available in the clinical/-medical sciences. When introduced into a living host using a suitable vehicle such as dimethyl sulfoxide (hereinafter "DMSO") or propylene glycol. These inhibitory compositions are useful for therapeutic treatment of ortho-static hypotension; hypotension; pain (algesia); renal function; allergic rhinitis; diabetic nephropathy; and as an aid in instances of poor perfusion of placentae. These kallikrein inhibitors are particularly effective in reversing angiooedema effects; and will act as an analgesic for pain and symptoms mediated by the release of kinins from the tissues. In addition, this novel class of tissue kallikrein inhibitors is especially useful as a co-drug for the control and reversal of clinical side-effects caused by the administration of known inhibitors against angiotensin converting enzyme (hereinafter "ACE"). In each instance, the administration of any embodiment of this class of tissue kallikrein inhibitors will cause diminished production of kinins in the body and provide the concomittant benefits obtainable through the reduction of vasoactive kinins.

The class of substrate analogues comprising the tissue kallikrein inhibitors of the present invention are most broadly defined by formulas I and II as stated below.

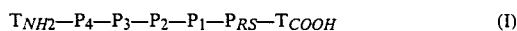

$$T_{NH2}-P_4-P_3-P_2-P_1-P_{RS}-T_{COOH} \quad (I)$$

$$P_3-P_2-P_1-P_{RS}-T_{COOH} \quad (II)$$

As is apparent from formulas I and II respectively, the substance of the novel inhibitors comprises a precise positioning of specific entities in sequence one to the other in which: $P_1$ represents the moiety at the designated number 1 position; $P_2$ represents the moiety at the designated number 2 position; $P_3$ represents the entity at the designated number 3 position; and $P_4$ represents an optional compound to be found at the designated number 4 positon respectively. Similarly, the $P_{RS}$ notation identifies the designated position for an individual recognition sequence of amino acid residues which serve to form and identify the catalytic cleavage site for tissue kallikreins. In addition, $T_{COOH}$ identifies the designated position of an optional moiety which is covalently bound to the carboxy terminal end of the molecule and is most desirable because it affects the physical properties (such as electrical charge) of the inhibitor molecule as a whole. $T_{NH2}$ is also a designated position which identifies an optional moiety bound to the N-terminal end of the inhibitor molecule which also effects the physical properties (electrical charge and the like) of the molecule as a whole.

For purposes of the present invention, the essence and most critical features of the tissue kallikrein inhibitors are those specific organic compositions utilized for $P_1$, $P_2$, and in particular $P_3$-within the designated sequences of formulas I and II respectively. For these reasons, each component designation will be described in detail, followed by the empirically obtained evidence which identifies and factually supports each designation.

The positioned entity $P_1$ is preferably an arginine residue or alternatively an effective arginine residue substitute. For purposes of the present invention, it will be recogized that lysine at the $P_1$ designated position is not adequate or useful as an arginine substitute. However, other linear amino acid residues, preferably of L-configuration, which carry a plurality of amine groups on the side chain linkage are deemed to be effective arginine residue substitutes; the fact that such substitutes are not naturally occuring is inconsequential to the invention.

Within this class of kallikrein inhibitors, it is desirable that the entity at $P_2$ be an amino acid residue comprising at least one ring configuration as part of its structure. It is most preferred that an L-amino acid residue be employed; the ring configuration, however, may be alicyclic, heterocyclic, or aromatic and it is inconsequential whether the chosen amino acid residue occurs in nature or not. Of the possible choices, the positioned $P_2$ entity is preferably selected from the group consisting of the following organic compositions: cyclohexylalanine (hereinafter "Cha"); leucine (hereinafter "Leu"); and phenylalanine (hereinafter "Phe").

The designated entity at $P_3$ can take a wide variety of different embodiments. The majority of unique and advantageous properties provided by this class of tissue kallikrein inhibitors is deemed to be the result of those organic compounds utilized as $P_3$. It is in all instances required that the $P_3$ embodiment be a bulky substance; that is—not a simple linear molecule, but rather a molecule which is branched or has a cyclic structure in some degree. It is also desirable that the composition used as $P_3$ comprise not less than 5 and not more than 15 carbon atoms which may be combined with one or more heteroatoms such as oxygen, nitrogen, sulfur, and the like in a variety of different configurations and structures.

In general, it is preferred that substances positioned at $P_3$ be in a D-configuration because this format does not appear to be subject to the same steric constraints such as the L-configuration of the same molecule. With this in mind, there are four categories of organic substances suitable for use as the designated $P_3$ composition. These include: First, branched amino acid residues without any ring configuration in its structure; this category is in fact an exception to the favored D-configuration because it has been empirically found that L-valine (hereinafter "Val") and L-isoleucine (hereinafter "Ile") provide more hydrolysis resistant embodiments than their D-configuration counterparts. Second, the $P_3$ entity can be an amino acid residue comprising at least 5 and not more than 15 carbon atoms, the residue having at least one alicyclic or aromatic ring configuration as part of its structure; specific embodiments within this category thus include phenylglycine (hereinafter "0Gly"), cyclohexylalanine (hereinafter "Cha"), and cyclohexylglycine (hereinafter "Chg"). Third, the $P_3$ entity can be a branched or alicyclic aliphatic compound comprising at least 5 and not more than 15 carbon atoms in its structure; specific examples of this category are cyclohexylacetic acid (hereinafter "Cxa") and 1-adamantanacetic acid (hereinafter "Ada"). Fourth, the $P_3$ designated entity can be an organic composition comprising at least 5 and not more than 15 carbon atoms, this composition having at least one aromatic ring configuration in its structure. A wide variety of specific embodiments of this category are well known, all of which contain at least one benzene ring. Of the four different categories for $P_3$, the embodiments comprising cyclohexylacetic acid or 1-adamantanacetic acid are most preferred.

The $P_4$ entity can be omitted entirely, but when present is a linear amino acid. In preferred embodiments, the $P_4$ designated position is omitted entirely. However, when present the specific amino acid serine (hereinafter "Ser") or its equivalent forms comprising at least one hydroxyl group are useful.

The designated $P_{RS}$ position identifies a recognition sequence of not more than three amino acids which serves as a lead-in sequence to identify the catalytic binding site for the tissue kallikrein enzyme; and in combination with the $P_1$ entity forms the cleavage or catalytic site upon which the tissue kallikrein enzyme acts. In preferred embodiments, the $P_{RS}$ entity is the sequence serine-valine-glutamine (hereinafter "Ser-Val-Gln"). It is expected however, that other amino acid residues alone or in sequence will function equally well in the inhibitor molecules represented by formulas I and II respectively. Accordingly, any amino acid sequences at the $P_{RS}$ position comprising not more than three amino acid residues which function to form and identify the catalytic cleavage site for tissue kallikreins are within the scope of the present invention.

The designated entities $T_{COOH}$ and $T_{NH2}$ individually are optional moieties which allow the tissue kallikrein inhibitors to be utilized in-vivo in a form which avoids adverse reactions in the body. These moieties provide two useful benefits: they act to enhance binding between the inhibitor molecule and the tissue kallikreins; and they make the inhibitor molecule as a whole more resistant to catabolism by amino and carboxyl peptidases, thus improving the half-life of the inhibitor in-vivo. $T_{COOH}$ can be omitted entirely if desired, but when present is a moiety such as an amine group which is bound to the carboxy (COOH)-terminal end of the molecule and which affects the physical properties such as the electrical charge of the inhibitor. When the preferred amine group becomes bound, it forms a resulting amide and alters the electrical charge at that end of the molecule. Similarly, the $T_{NH2}$ can be omitted entirely, but when present is bound to the amino (NH$_2$)-terminal end of the inhibitor; a preferred substance for use is acetic acid, which after binding to the inhibitor molecule forms an acetyl moiety which alters the electrical charge properties at the N-terminal end of the molecule. The use of $T_{COOH}$ and $T_{NH2}$ moieties allows the user to disperse concentrations of specific tissue kallikrein inhibitors in various fluid carriers and thus also provides the means for easy administration of specific inhibitor embodiments to the subject in-vivo.

Synthesis Of Tissue Kallikrein Inhibitors

The class of tissue kallikrein inhibitors defined by formulas I and II above are preferably synthesized, purified, and characterized using the micromethods conventionally known for preparation of IgA1 protease inhibitors adapted from Malison et al. ["Inhibition of IgA1 Protease With Immunoglobulin Hinge Region Dimers", in *Peptides: Structure and Function* (Hruvy and Rich, editors), Pierce Chemical Company, Rockford, Ill., 1984, pages 627–630].

In short, the inhibitor peptide sequences are prepared by solid phase synthesis. For peptide amides, the protected carboxy-terminal amino acid will be coupled to 4-methylbenzhydrylamine (3.0 grams, 1.3 nMol NH$_2$) using dicyclohexylcarbodiimide. After testing with ninhydrin for completeness of the coupling, the aminoacyl polymer is deprotected using 6N HCl/dioxane; neutralized with 5% $(CH_3CH_2)_3N/CH_2Cl_2$; and coupled to the penultimate amino acid residue. This cycle is repeated until the desired number of amino acid residues have been added. Testing for completeness of coupling is done after addition of every residue. After addition of the amino-terminal acetyl group as $(CH_3CO)_2O/(CH_3CH_2)_N$, the peptidyl resin is treated with HCl/dioxane to remove ionically bound impurities, washed repeatedly with $CH_3CH_2OH$ and $CH_2Cl_2$, and dried to constant weight.

The peptidyl-resin is then treated with HF/10% anisole for one hour at 0 C. to deprotect and cleave the peptide from the support. After evaporation of the HF/anisole, the resin is extracted sequentially with ethyl acetate and a series of successive 1%, 5%, 10%, and 25% acetic acid solutions. The extracts are then lyophilized.

For purposes of empirical investigation as will be described hereinafter, a tritiated amino acid is added during the course of synthesis to simply quantitation of the peptide inhibitor in subsequent experiments. This is accomplished by adding the protected labeled amino acid (such as Boc-[$^3$H]Phe) to the coupling mixture. Tritiated amino acid derivatives (0.1Ci/Mol) are prepared by reacting the labeled amino acid with di-t-butyldicarbonate (Tridom, Hauppage, N.Y.). The peptidyl-resin is then treated to cleave the resin from the support and extracted sequentially as previously described above. The extracts are counted and those containing radioactive label are pooled and lyophilized.

All lyophilized peptide extracts, whether radiolabeled or not, are then dissolved in acetic acid solution (1–25% v/v) and gel filtered on the appropriate Sephadex column in the same solvent. The eluant is collected; the fractions counted; ultraviolet absorbance measured; and the results plotted. The fractions containing peptide are then pooled and lyophilized. The homogeneity of the gel filtered peptide is judged by reversed phase HPLC and, if necessary, the peptide purified to homogenity by conventional preparative HPLC techniques.

It is recognized that in order to prepare the preferred embodiments utilizing cyclohexylacetic acid or 1-adamantaneacetic acid at the $P_3$ position, some modification of the above synthesis procedure is required. Because the formed inhibitor molecules incorporating Cxa or Ada are poorly soluble in 1% (v/v) acetic acid, the extraction with 10% acetic acid was followed by an extraction with absolute ethanol; this is done after cleavage to increase the yield. For the same reason, gel filtration on Sephadex is omitted; instead, the acetic acid and ethanol extracts are combined, subjected to rotary evaporation to remove the ethanol, and lyophilized. Subsequently, each preparation was individually dissolved in dimethylsulfoxide (DMSO), and further purified by isocratic elution from a reverse phase high performance liquid chromatography (HPLC) preparatory column (Synchropak RP-P) as previously described above. Each of these inhibitor molecules were then subjected to HPLC analysis using an Altex ultrasphere ODS column using an aqueous $CH_3CN$—$CF_3COOH$ (20–70% in 30 minutes) gradient elution system. Each yielded a single peak of absorbance at A=220 which demonstrated its purity.

It is recognized that the tissue kallikrein inhibitors comprising the present invention are expected to be administered to the living subject as a sterile infusion fluid. In the experimental series which follows herein, DMSO served as the infusion vehicle or carrier. It is recognized and expected, however, that other infusion fluids commonly known and used for this purpose are equally useful and available; and, furthermore that the choice of an infusion fluid is merely a question of personal preference or convenience to the user. For these reasons, any liquid which is suitable for use as a sterilizable infusion fluid without adverse reaction to the living host and which is able to carry the tissue kallikrein inhibitor compositions defined above, are deemed to be within the scope of the present invention.

In order to demonstrate and empirically document the range of substances useful at each of the designated positions when synthesizing embodiments of the tissue kallikrein inhibitors and to provide evidence of the effectiveness of this class of inhibitors comprising the present invention, a series of experiments were undertaken. It will be expressly recognized and appreciated, however, that the empirical data obtained for each specific embodiment of the present invention is merely illustrative of the subject matter as a whole comprising the present invention; and further, such empirical evidence neither restricts nor limits the class of tissue kallikrein inhibitors to the specific embodiments described or evaluated within the experiments themselves. With this understanding in mind, each of the experiments will be described and evaluated individually.

Experimental Series I

Human urinary kallikrein (hereinafter "HUK") was highly purified using a modification of published methods that employ ultrafiltration, aprotinin-CH-sepharose affinity chromatography, and Sephadex G-100 gel filtration [ole-MoiYoi et al., Proc. Natl. Acad. Sci. USA 76: 3121–3125 (1979)]. A minor contaminant with [$^{14}$C] hemoglobin cleaving activity was separated by eluting the affinity column with 80 ml of $NaOCOCH_3$ (pH 5.6) and then with a pH gradient made from 50 ml of 0.1M $NaOCOCH_3$ (pH 5.6) and 150 ml of 0.1M $NaOCOCH_3$ (pH 3.0). The pH of each fraction was determined immediately upon elution, and the fraction was neutralized by addition of 2.0 ml of 2M Tris-HCL buffer (pH 8.0).

The determination of the Michaelis constant ($K_M$), inhibitor constant ($K_I$), and the maximum velocity of hydrolysis ($V_{max}$) of individual substrate analogue inhibitors was performed in the following manner.

$K_M$ Determination: Hydrolysis of the substrate analogue inhibitors by HUK was measured by combining the test inhibitor at different concentrations on either side of the $K_M$ value with the enzyme at pH 9.0 for thirty minutes at 37 C. The cleavage products were separated from the starting material in the digest by HPLC on a Beckman octadecylsilane (ODS) column (1×25 cm) using a thirty minute gradient of from 0–70% $CH_3CN$ in triethylammonium phosphate buffer (pH 7.0). The starting materials and reaction products were completely resolved under these conditions. Absorbance of the HPLC effluent was monitored at 220 nm. Individual fractions were collected and the amount of peptide degradation products was quantitated by counting in a liquid scintillation counter. Samples containing individual inhibitors were incubated without HUK and solvent blanks were also chromatographed and analyzed in the same way. Control runs in which the entire HPLC effluent was collected as a series of 10 fractions demonstrated that greater than 95% of the applied radioactivity was recovered and the expected products of kallikrein cleavage were not further degradated into smaller peptides.

For test purposes, in these HUA cleavage studies, individual peptide sequences were synthesized, purified, and characterized as previously described herein. For these cleavage studies, doubly labelled peptides were prepared using [$^3$H]-valine and [$^3$H]-proline respectively. In addition, 6.0N HCL-dioxane was used for removal of tert-butoxycarbonyl protecting groups and 90% hydrogen fluoride/10% anisole (volume/volume) for global deprotection on completion of the synthesis. After extraction and gel filtration on Sephadex G-15, final purification was completed by isocratic elution from a synchrom RP-P column (2.1×25 cm) with $CH_3CN$—$H_2O$ (8 ml/min). The resultant peptides were deemed to be homogeneous by amino acid analysis;

high performance liquid chromatography; thin layer chromatography; and $A_{230}/A_{260}$ ratio analysis.

$K_I$ Determinations: $K_I$ measurements were performed using a HP8450A diode array spectrophotometer (Hewlett Packard; Palo Alto, Calif.) attached to a Model 216 computer using the multi-component assay program modified to allow simultaneous determination of reaction velocity in four samples. Dixon plots were used to data reduction and for calculation of $V_{max}$. The substrate analogues were examined for inhibition of the capacity of HUK to cleave p-nitroaniline from the chromogenic substrate S2266 comprising D-Val-Leu-Arg-p-nitroanilide (Kabi; Stockholm, Sweden) at pH 9.0 and 37 C. Inhibition of biologically active kinin from LMW-kininogen was done at pH 7.7 and 37 C.

Procedurally, the $K_I$ values for the preliminary analogue inhibitors reported previously [Okunishi et al., *Hypertension* 7 (Suppl. I): I-72-I-75 (1985)] were determined by adding the chromogenic substrate S-2266 comprising D-Val-Leu-Arg-4-nitroaniline to a mixture of the analogue inhibitor and the HUK. The results are given in Table I below.

these substrate analogues are required before 50% inhibition is achieved.

Clearly, therefore, these preliminary substrate analogue inhibitors are unsuitable for use in-vivo because of their rapid cleavage by HUK; and by their relatively moderate ability to inhibit HUK individually and as a group.

Experimental Series II

An evaluation of other possible peptide sequences and their potential effect as substrate analogue inhibitors specifically of tissue kallikrein was undertaken using chromogenic substrates comprising alternate series of tripeptide 4-nitroanilides using previously described methods [Amundsen et al., "Methods For The Determination Of Glandular Kallikrein By Means Of A Chromogenic Tripeptide Substrate," in *Kinins-II*. Part A. Plenum Press, 1979, pages 83-95]. This methodology relies on the capacity of HUK to cleave p-nitroaniline from specifically synthesized tripeptide 4-nitroanilines. Controls for this experimental series included S-2266 comprising D-Val-Leu-Arg-4NA; S-2444 comprising

TABLE I

| ANALOGUE SUBSTRATE | (N—TERMINAL-COOH—TERMINAL) FORMULA | $K_I$ (um) | $K_M$ (um) | TURNOVER NO. (mol/mol/sec) | RELATIVE SPECIFICITY |
|---|---|---|---|---|---|
| KKI-4 | Ac—Phe—Arg—Ser—Val—Gln—NH$_2$ | 35 | 307 | 188 | 4.2 |
| KKI-5 | Ac—Pro—Phe—Arg—Ser—Val—Gln—NH$_2$ | 156 | 482 | 229 | 3.2 |
| KKI-6 | Ac—Ser—Pro—Phe—Arg—Ser—Val—Gln—NH$_2$ | 73 | 37.6 | 249 | 45.4 |
| LMN kininogen | (approx. 50,000 daltons) | — | 12.5 | 1.83 | 1.0 |

As shown by the data of Table I, these preliminary analogue inhibitors are rapidly cleaved by HUK. A quantitative assessment of the capacity of these specific analogue inhibitors is shown by the $K_M$; the turnover number; and the relative specificity for each of these previously reported substrate analogues. As shown, KKI-6 has a $K_m$ of 37.6 um, which is approximately three times that obtained using single-chain, fully active, low molecular weight (LMW) kininogen. The $K_m$ values for KKI-5 of 482 um and for KKI-4 of 307 um are about one order of magnitude larger. The turnover numbers for all three substrate analogues are approximately two orders of magnitude greater (188-249 mol/molsec) than those previously obtained for human LMW kininogen. Enzyme specificity, which relates turnover number to the concentration of free enzyme, appears greatest for KKI-6 and less for the other analogue inhibitors.

In addition, note that the $K_I$ values for KKI-4, -5, and -6 were 35, 136, and 73 um respectively; these values demonstrate that relatively large concentrations of D-Glu-Gly-Arg-4NA; and S-2302 comprising D-Pro-Phe-Arg-4NA respectively. The 50% inhibitory concentration (IC$_{50}$) values for each synthesized tripeptide 4-nitroanilide was determined at 37 C. at pH 9.0 using the specific kallikrein substrates S-2266 (Kabi, Helena Laboratories, Beaumont, Tex.). 4.0 nanograms (hereinafter "ng") of HUK were used in each sample. Blanks lacking S-2266 were run in parallel to correct for hydrolysis of all samples. In all cases, the amount of 4-nitroaniline generated from each tripeptide was less than 10% of that observed for the hydrolysis of S-2266.

Subsequently, the $K_m$ and $V_{max}$ for each test tripeptide 4-nitroanilide was determined using conventional techniques in an HP-8450 diode array spectrophotometer (Hewlett Packard Company) attached to a HP-85 microcomputer. The multicomponent assay program was modified to allow the simultaneous determination of the reaction velocity in four samples. The results of this experimental series are presented in Table II below.

TABLE II

| (N—COOH) FORMULA | IC$_{50}$ (um) | $K_M$ (um) | $V_{max}$ ($10^{-7}$m/min) | RELATIVE SPECIFICITY |
|---|---|---|---|---|
| P$_3$—P$_2$—P$_1$— | | | | |
| D-Chg—Cha—Arg—4NA | 2.1 | 0.82 | 1.39 | 121 |
| D-Chg—Phe—Arg—4NA | 3.7 | 0.84 | 0.33 | 28 |
| L-Val—Cha—Arg—4NA | 4.1 | 0.17 | 0.81 | 333 |
| D-Chg—Leu—Arg—4NA | 5.9 | 0.98 | 0.32 | 23 |
| D-0Gly—Cha—Arg—4NA | 7.4 | 1.96 | 1.59 | 58 |
| L-Ile—Cha—Arg—4NA | 10.5 | 1.33 | 0.84 | 45 |
| L-Chg—Cha—Arg—4NA | 11.5 | 12.52 | 0.63 | 3.6 |
| D-Chg—Pro—Arg—4NA | 16.0 | 4.80 | 0.32 | 4.8 |
| L-Chg—Leu—Arg—4NA | 18.7 | * | * | — |
| D-Chg—Cha—Lys—4NA | 150 | 46.64 | 0.93 | 1.4 |

TABLE II-continued

| (N—COOH) FORMULA | IC$_{50}$ (um) | K$_M$ (um) | V$_{max}$ ($10^{-7}$m/min) | RELATIVE SPECIFICITY |
|---|---|---|---|---|
| D-0Gly—Cha—Lys—4NA | >200 | 48.06 | 0.69 | 1 |

*No hydrolysis observed;
IC$_{50}$ = 50% inhibitory concentration;
K$_M$ = Michaelis constant;
V$_{max}$ = maximum velocity;
Chg = cyclohexylglycine;
Cha = cyclohexylalanine;
0Gly = phenylglycine;
4NA = 4-nitroaniline (p-nitroaniline)

The data of Table II demonstrates that 4-nitroanilides are hydrolyzed slowly by HUK; yet their capacity to inhibit S-2266 cleavage indicates that they have much improved affinities for the HUK enzyme. A comparison of the series P$_3$-Cha-Arg-4NA indicates that when P$_3$ as the L-configuration, an inverse relationship between size and affinity exists. The reverse affect is seen when the amino acid residue at the designated P$_3$ position has the opposite (D-) stereoisomerism. This demonstrates that HUK can accomodate a large, bulky, side chain or ring having the D-configuration rather than the L-configuration at the P$_3$ position. Note that this steric restraint is not observed and thus not required at the designated P$_2$ position, thereby allowing a much greater choice of amino acid residues and other organic molecules at this position. It is also noteworthy that for a useful degree of inhibition to occur, an arginine residue or a molecule having multiple amine groups in its side chain configuration is required; in each instance, greater inhibition is observed with an arginine residue than when using a lysine residue.

The data shown in Table II clearly indicates that tripeptide nitroanilides bind tightly to HUK and are only slowly cleaved by tissue kallikrein. This clearly different from those preliminary substrate analogues evaluated previously and indicates that it is preferable to utilize peptides of specific sizes and characteristics in each of the designated P$_3$ and P$_2$ positions other than those naturally found in nature.

Experimental Series III

Hexapeptide analogue inhibitors were synthesized as previously described herein, incorporating cyclohexylacetic acid (Cxa) or 1-adamantaneacetic acid (Ada), alicyclic organic compositions, at the designated P$_3$ position. For test purposes, [$^3$H]valine was incorporated into the recognition sequence comprising serine-valine-glutamic acid-amide (Ser-Val-Glu-NH$_2$). The Cxa containing inhibitor molecule is identified as KKI-7 and comprises the sequence Cha-Phe-Arg-Ser-Val-Gln-NH$_2$; similarly, the Ada inhibitory molecule is identified as KKI-8 and comprises the sequence Ada-Phe-Arg-Ser-Val-Gln-NH$_2$.

Initially, the inhibitor constant (K$_I$) for each of these novel inhibitor compositions was determined using purified HUK and the tripeptide nitroanilide, S-2266. The ability to inhibit hydrolysis of the S-2266 substrate was performed in 50 mM tris-HCL buffer (pH 9.0) at 37 C. Subsequently, the ability of these novel inhibitors to inhibit human plasma kallikrein and bovine pancreatic trypsin were similarly examined using the specific substrates H-D-Pro-Phe-Arg-p-nitroanilide (S-2302) and Glu-Gly-Arg-p-nitroanilide (S-2444) respectively. The degradation products of each series was purified by HPLC and quantified by liquid scintillation counting as previously described. The results are given by Table III below.

TABLE III

| | K$_1$ (micromolar) | |
|---|---|---|
| ENZYME | KKI-7 | KKI-8 |
| Human Urinary Kallikrein | 4.0 | 4.2 |
| Human Plasma Kallikrein | 244 | 358 |
| Trypsin | 12.3 | 71.8 |

KKI-7: Cha—Phe—Arg—Ser—Val—Gln—NH$_2$;
KKI-8: Ada—Phe—Arg—Ser—Val—Gln—NH$_2$;
Formula II: P$_3$—P$_2$—P$_1$—(P$_{RS}$)—T$_{COOH}$ The data of Table III clearly indicates that the KKI-7, and -8 inhibitors are specific for tissue kallikreins and are not effective inhibitors of either plasma kallikrein or trypsin. Equally important, the observed K$_I$ values for KKI-7 and KKI-8 of 4.0 and 4.2 uM respectively are far smaller values than those obtained for the preliminary substrate analogues of Table I; clearly, these novel inhibitors comprising Cxa and Ada at the P$_3$ designated position are far more effective inhibitors than those previously synthesized and evaluated in the published literature. Equally important, analysis of the reaction products indicate that KKI-7 and KKI-8 are cleaved by HUK at approximately 15% the rate at which hexapeptides containing proline in the P$_3$ position are cleaved.

Experimental Series IV

A series of in-vivo studies were undertaken to determine the effective of the KKI-7 and KKI-8 inhibitors on the blood pressure response to glandular kallikrein. Initially, three female Dahl hypertension-resistant rats (Brookhaven Laboratories, Brookhaven, N.Y.), and four male Sprague-Dewley rats (Charles River, Wilmington, Mass.) were utilized. Each of these animals was anesthetized with Inactin (100 mg/kg ip) and cannulated in a femoral artery with PE-50 polyethylene tubing (Clay Adams, Parsippany, N.J.) which was connected to a Hewlett-Packard model 1280 blood pressure transducer and model 7702B recorder. The right jugular vein was cannulated with PE-10 tubing. The rats were tracheostomized, but respiration was not artificially assisted. Rat urinary kallikrein (hereinafter "RUK") was repeatedly administered via a venous cannula until a reproducable response was obtained. KKI-8 inhibitor was then infused using a Harvard model 901 infusion pump at a rate of 32 nmol/0.022 ml/min. RUK (203.5 ng in 50 ul) was injected during the infusion period. After the infusion was stopped, the reversibility of the inhibition was examined by further injections of RUK. The infusion of KKI-8 (32 nmol/min/animal) inhibited the very gradual and modest decrease in blood pressure otherwise elicited with RUK.

In order to develop a more reproducible, less tachyphylactic system, a rat blood flow model was developed and assessed in male Sprague-Dawley rats. These animals were anesthetized subcutaneously with urethane (1.4 g/kg). Polyethylene PE-10 tubing was inserted into the right femoral artery and femoral vein for intra-arterial and intravenous injections, respectively, the arterial catheter was inserted such that the tip was located immediately proximal to the bifurcation. The rats were tracheostomized and cannulated with PE-200 tubing. A subcutaneous 23 gauge needle was left in the back of the animal for booster injections of urethane (0.35 g/kg every 2.5 hours). A blood flow probe (1.5 mm circumference) was placed on the left femoroal artery and the mean femoral arterial blood flow was monitored with a square-wave electromagnetic flowmeter (Carolina Medical Electronics, model 501). Rat submaxillary gland kallikrein (hereinafter "RSK") or porcine pancreatic kallikrein (hereinafter "PPK") was given intra-arterially, unless otherwise indicated, until a reproducible response was obtained. Each animal was then infused intravenously with KKI-7 inhibitor in DMSO (206 nmole/0.022 ml/min) or with the DMSO vehicle (0.022 ml/min). Bradykinin was also given intra-arterially to determine whether or not the KKI-7 inhibitor effected the blood flow response to bradykinin. The magnitude and duration of the responses to PPK, RSK, and bradykinin were compared before, during, and after the intravenous infusion of KKI-7 or the DMSO vehicle alone. The blood flow increase over the basal blood flow was integrated and expressed as arbitrary units or as the percent change from blood flow increased observed during the control period. The results are provided by FIG. 1 and Table IV below.

TABLE IV

| | | CHANGE IN BLOOD FLOW (% OF CONTROL) | | | |
|---|---|---|---|---|---|
| | | DURING INFUSION | | AFTER INFUSION | |
| Infused: | Injected: | <10 min | 10-30 min | <10 min | 30-60 min |
| KKI-7 | RSK | 52% (n = 3) | 16% (n = 2) | 11% (n = 1) | 35% (n = 1) |
| | PPK | 38% (n = 1) | 31% (n = 1) | | 52% (n = 1) |
| | BK | 95% (n = 2) | | | |
| DMSO | RSK | 98% (n = 2) | | 94% (n = 1) | |
| | BK | 100% (n = 2) | | | |

KKI-7, Cha—Phe—Arg—Ser—Val—Gln—NH$_2$; DMSO, dimethylsulfoxide; RSK, rat submaxillary gland kallikrein; PPK, porcine pancreatic kallikrein; BK, bradykinin Empirically, the injection of 20-50 ng of RSK over a period of 5-10 seconds elicited a biphasic response that usually lasted for 1.5-2.0 minutes. This is illustrated by FIG. 1. The infusion of KKI-7 reduces the second phase of the response to 6% or 26% (average 16%) of the control value when RSK was reinjected at a time 10-30 minutes after the infusion was started. Within the first ten minutes after the KKI-7 inhibitor infusion was begun, RSK injections produced approximately one-half of the control response (49-56%). Results from one of the animals injected with RSK shows that this response is relatively long lived. The response to the injection of 2 units of PPK is also reduced during and after infusion with KKI-7 while the response to 1-2 ng of bradykinin injected during the inhibitor infusion was not. In comparison, infusion of the DMSO vehicle alone, at the same rate at which KKI-7 was infused, lead only to a transient increase in blood flow as illustrated by FIG. 1, but did not alter the animal response to the injection of RSK or bradykinin.

Overall, therefore, the KKI-7 inhibitor was effective against both RSK and PPK in-vivo and had no affect on the response to bradykinin. Equally important, the infusion of KKI-7 in the DMSO vehicle, as well as infusion of the DMSO vehicle itself, led only to a moderate, transient increase in blood flow. No specific side-effects of infusing KKI-7 were observed during the experimental period and the blood flow responses to RSK and PPK returned toward the normal, control responses after the infusion was terminated.

Figure 2:
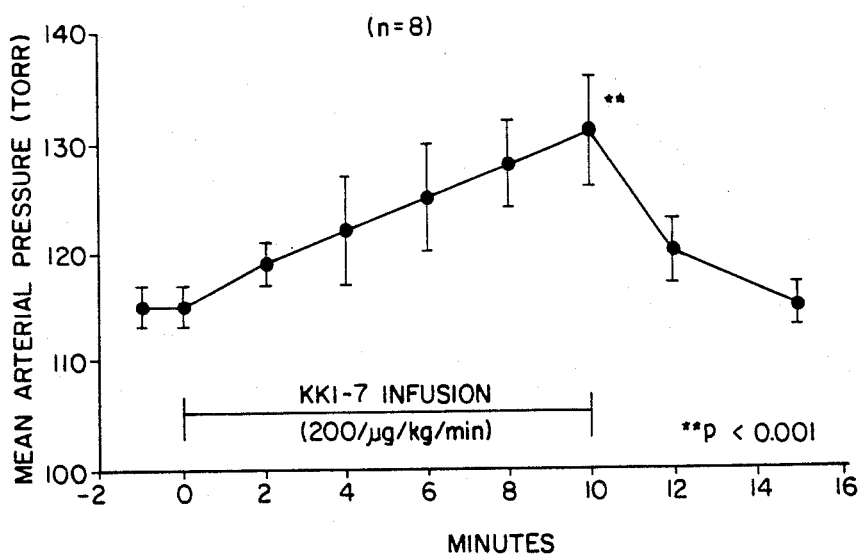
FIG. 2 is a graph illustrating the increase in blood pressure over time caused by an infusion of a preferred embodiment of the present invention.
Figure 3:
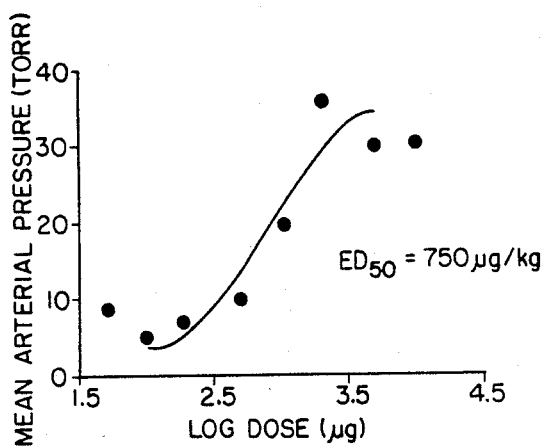
FIG. 3 is a graph illustrating the log dose-response effect on blood pressure of a preferred embodiment of the present invention when administered as a bolus injection.

Subsequently, a third study utilizing normotensive, salt-replete rats was performed employing an infusion of KKI-7 at a rate of 200 ug of inhibitor per kilogram of rat per minute (200 ug/kg/min). Eight rats each received this infusion for 15 minutes during which the change in mean arterial blood pressure (Torr) was monitored. The results are provided by FIG. 2. In addition, a series of bolus injections were given to conscious, salt-replete, normotensive rats to determine the ED$_{50}$ dosage necessary to cause a substantive increase in blood pressure. The results are graphically illustrated by FIG. 3 as the log-dose response effect of KKI-7 upon blood pressure. The calculated ED$_{50}$ dose is 750 ug/kg. By these data, it is abundantly clear and unequivocally demonstrated that KKI-7 induces substantial increases in blood mean arterial blood pressure when administered either as a bolus injection or as an infusion.

The invention is not to be restricted in form or limited in scope except by the claims appended hereto.

What I claim is:

1. A class of tissue kallikrein inhibitors comprising the formula sequence:

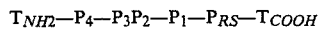

$$T_{NH2}-P_4-P_3P_2-P_1-P_{RS}-T_{COOH}$$

wherein

P$_1$ is an amino acid residue selected from the group consisting of arginine residues and arginine residue analogues having a plurality of nitrogen atoms in its side chain linkage;

P$_2$ is an amino acid residue comprising at least one ring configuration of not more than 6 carbon atoms in its structure;

P$_3$ is a branched amino acid residue comprising at least 5 and not more than 15 carbon atoms and is without any ring configuration in its structure;

P$_4$ can be omitted entirely, but when present is a amino acid residue selected from the group consisting of serine and serine analogues having at last one hydroxyl group in its structure;

P$_{RS}$ is a recognition sequence comprising not more than three amino acid residues wherein at least one amino acid residue in said recognition sequence is selected from the group consisting of serine, valine, and glutamine and wherein said recognition sequence serves to identify the catalytic cleavage site for the tissue kallikrein;

T$_{COOH}$ can be omitted entirely, but when present is a non-amino acid moiety reactive with and binding to the carboxy-terminal end of said sequence, said moiety altering the electrical charge properties of the inhibitor; and T$_{NH2}$ can be omitted, but when present is a non-amino acid moiety reactive with and binding to the amino-terminal end of said sequence, said moiety altering the electrical charge properties of the inhibitor.

2. A class of tissue kallikrein inhibitors comprising the formula sequence:

$T_{NH2}—P_4—P_3—P_2—P_1—P_{RS}—T_{COOH}$ wherein
- $P_1$ is an amino acid residue selected from the group consisting of arginine residues and arginine residue analogues having a plurality of nitrogen atoms in its side chain linkage;
- $P_2$ is an amino acid residue comprising at least one ring configuration of not more than 6 carbon atoms in its structure;
- $P_3$ is an amino acid residue comprising at least 5 and not more than 15 carbon atoms and has at least one configuration selected from the group consisting of alicyclic ring configurations and aromatic ring configurations in its structure;
- $P_4$ can be omitted entirely, but when present is a amino acid residue selected from the group consisting of serine and serine analogues having at least one hydroxyl group in its structure;
- $P_{RS}$ is a recognition sequence comprising not more than three amino acid residues wherein at least one amino acid residue in said recognition sequence is selected from the group consisting of serine, valine, and glutamine and wherein said recognition sequence serves to identify the catalytic cleavage site for the tissue kallikrein;
- $T_{COOH}$ can be omitted entirely, but when present is a non-amino acid moiety reactive with and binding to the carboxy-terminal end of said sequence, said moiety altering the electrical charge properties of the inhibitor; and
- $T_{NH2}$ can be omitted, but when present is a non-amino acid moiety reactive with and binding to the amino-terminal end of said sequence, said moiety altering the electrical charge properties of the inhibitor.

3. A class of tissue kallikrein inhibitors comprising the formula sequence:

$P_3—P_2—P_1—P_{RS}—T_{COOH}$ wherein
- $P_1$ is an amino acid residue selected from the group consisting of arginine residues and arginine residue analogues having a plurality of nitrogen atoms in its side chain linkage;
- $P_2$ is an amino acid residue comprising at least one ring configuration of not more than 6 carbon atoms in its structure;
- $P_3$ is a branched compound comprising at least 5 and not more than 15 carbon atoms in its structure and is selected from the group consisting of aliphatic compounds and alicyclic compounds;
- $P_{RS}$ is a recognition sequence comprising not more than three amino acid residues wherein at least one amino acid residue in said recognition sequence is selected from the group consisting of serine, valine, and glutamine and wherein said recognition sequence serves to identify the catalytic cleavage site for the tissue kallikrein; and
- $T_{COOH}$ can be omitted entirely, but when present is a non-amino acid moiety reactive with and binding to the carboxy-terminal end of said sequence, said moiety altering the electrical charge properties of the inhibitor.

4. A class of tissue kallikrein inhibitors comprising the formula sequence:

$P_3—P_2—P_1—P_{RS}—T_{COOH}$ wherein
- $P_1$ is an amino acid residue selected from the group consisting of arginine residues and arginine residue analogues having a plurality of nitrogen atoms in its side chain linkage;
- $P_2$ is an amino acid residue comprising at least one ring configuration of not more than 6 carbon atoms in its structure;
- $P_3$ is an organic composition comprising at least 5 and not more than 15 caron atoms and has at least one aromatic ring configuration in its structure;
- $P_{RS}$ is a recognition sequence comprising not more than three amino acid residues wherein at least one amino acid residue in said recognition sequence is selected from the group consisting of serine, valine, and glutamine and wherein said recognition sequence serves to identify the catalytic cleavage site for the tissue kallikrein; and
- $T_{COOH}$ can be omitted entirely, but when present is a non-amino acid moiety reactive with and binding to the carboxy-terminal end of the said sequence, said moiety altering the electrical charge properties of the inhibitor.

5. The class of tissue kallekrein inhibitors as recited in claim 1, 2, 3, or 4 wherein $P_1$ has a L-configuration.

6. The class of tissue kallekrein inhibitors as recited in claim 1, 2, 3, or 4 wherein $P_2$ has a L-configuration.

7. The class of tissue kallekrein inhibitors as recited in claim 1, 2, 3, or 4 where $P_3$ has a D-configuration.

8. A class of tissue kallikrein inhibitors as recited in claims 1, 2, 3, or 4 wherein $P_2$ is selected from the group consisting of cyclohexylalanine, phenylalanine, proline, and cyclohexylglycine.

9. A class of tissue kallikrein inhibitors as recited in claims 1, 2, 3, or 4 wherein $P_{RS}$ comprises the sequence serine-valine-glutamine.

10. A class of tissue kallikrein inhibitors as recited in claims 1, 2, 3, or 4 wherein $T_{COOH}$ is an amine group.

11. A class of tissue kallikrein inhibitors as recited in claims 1 or 2 wherein $T_{NH2}$ is an acetyl group.

12. A class of tissue kallikrein inhibitors as recited in claim 1 wherein $P_3$ is selected from the group consisting of valine and isoleucine residues.

13. A class of tissue kallikrein inhibitors as recited in claim 2 wherein $P_3$ is selected from the group consisting of cyclohexylglycine, cyclohexylalanine, and phenylglycine residues.

14. A class of tissue kallikrein inhibitors as recited in claim 3 wherein $P_3$ is selected from the group consisting of cyclohexylacetic acid and 1-adamantaneacetic acid.

15. A class of tissue kallikrein inhibitors as recited in claims 1, 2, 3, or 4 wherein said inhibitors are dispersed in an infusion vehicle.

16. A class of tissue kallikrein inhibitors as recited in claim 15 wherein said infusion vehicle is dimethylsulfoxide.

* * * * *